United States Patent
Choi et al.

(10) Patent No.: US 9,505,678 B2
(45) Date of Patent: Nov. 29, 2016

(54) PROCESS TO PRODUCE AROMATICS FROM CRUDE OIL

(71) Applicant: Saudi Arabian Oil Company, Dhahran (SA)

(72) Inventors: Ki-Hyouk Choi, Dhahran (SA); Joo-Hyeong Lee, Ras Tanura (SA); Emad N. Shafei, Saihat (SA); Faisal M. Al-Faqeer, Dammam (SA)

(73) Assignee: SAUDI ARABIAN OIL COMPANY (SA)

( * ) Notice: Subject to any disclaimer, the term of this patent is extended or adjusted under 35 U.S.C. 154(b) by 201 days.

(21) Appl. No.: 14/274,806

(22) Filed: May 12, 2014

(65) Prior Publication Data

US 2015/0321975 A1   Nov. 12, 2015

(51) Int. Cl.
  *C07C 4/04* (2006.01)
  *C07C 7/04* (2006.01)
  *C07C 7/10* (2006.01)
  (Continued)

(52) U.S. Cl.
  CPC ............... *C07C 4/04* (2013.01); *C07C 7/005* (2013.01); *C07C 7/10* (2013.01); *C10G 9/00* (2013.01); *C10G 9/002* (2013.01); *C10G 21/00* (2013.01); *C10G 33/00* (2013.01); *C10G 55/04* (2013.01); *C10G 2300/4006* (2013.01); *C10G 2300/4012* (2013.01); *C10G 2400/30* (2013.01)

(58) Field of Classification Search
  None
  See application file for complete search history.

(56) References Cited

U.S. PATENT DOCUMENTS 3,690,706 A    9/1972  Boik et al.
4,571,295 A *  2/1986  Forte ............... C10G 21/28
                                              208/321

(Continued)

FOREIGN PATENT DOCUMENTS

WO   2009/073446 A2   6/2009
WO   2011/132056 A2   10/2011
WO   2013/066852 A2   5/2013

OTHER PUBLICATIONS

PCT International Search Report and The Written Opinion of the International Searching Authority dated Aug. 28, 2015; International Application No. PCT/US2015/030261; International Filing Date: May 12, 2015.

(Continued)

*Primary Examiner* — In Suk Bullock
*Assistant Examiner* — Philip Louie
(74) *Attorney, Agent, or Firm* — Bracewell LLP; Constance Gall Rhebergen

(57) ABSTRACT

A process for producing aromatics from a hydrocarbon source in the presence of supercritical water comprising the steps of mixing a pressurized, pre-heated water stream with a pressurized, pre-heated petroleum feedstock, the pressurized, pre-heated water stream at a pressure above the critical pressure of water and a temperature above the critical temperature of water, feeding the combined stream to a supercritical water reactor to create a modified stream, cooling and depressurizing the modified stream, separating the depressurized stream in a vapor-liquid separator, condensing the vapor stream, separating the condensed stream into a water recovery stream and a light product recovery stream, extracting the aromatics from the light product recovery stream, depressurizing the liquid stream, separating the depressurized liquid stream in a heavy separator into an upgraded product stream, and recycling part of the upgraded product stream to the pressurized, pre-heated petroleum feedstock as a product recycle.

13 Claims, 3 Drawing Sheets

(51) Int. Cl.
*C07C 7/00* (2006.01)
*C10G 33/00* (2006.01)
*C10G 55/04* (2006.01)
*C10G 9/00* (2006.01)
*C10G 21/00* (2006.01)

(56) References Cited

U.S. PATENT DOCUMENTS

| | | | |
|---|---|---|---|
| 4,840,725 | A | 6/1989 | Paspek |
| 7,754,067 | B2 * | 7/2010 | Allam .................... B01F 5/0604 208/107 |
| 7,922,895 | B2 | 4/2011 | Banerjee |
| 2002/0086150 | A1 * | 7/2002 | Hazlebeck ............ C23C 28/023 428/304.4 |
| 2003/0168381 | A1 | 9/2003 | Hokari et al. |
| 2007/0056881 | A1 | 3/2007 | Berkowitz et al. |
| 2009/0139715 | A1 | 6/2009 | Choi |
| 2009/0159498 | A1 * | 6/2009 | Chinn ..................... C10G 9/00 208/85 |
| 2009/0159504 | A1 | 6/2009 | Choi et al. |
| 2009/0166261 | A1 | 7/2009 | Li et al. |
| 2009/0206006 | A1 | 8/2009 | Allam |
| 2009/0314683 | A1 | 12/2009 | Matsushita |
| 2010/0314583 | A1 * | 12/2010 | Banerjee ................ C10G 11/16 252/373 |
| 2011/0163011 | A1 * | 7/2011 | Yarbro ................... C10G 1/047 208/298 |
| 2012/0000819 | A1 | 1/2012 | Matsushita |
| 2012/0061294 | A1 * | 3/2012 | Choi ..................... C10G 47/32 208/97 |
| 2012/0181217 | A1 | 7/2012 | Choi et al. |
| 2013/0140214 | A1 | 6/2013 | Choi |
| 2014/0109465 | A1 | 4/2014 | Coppola et al. |

OTHER PUBLICATIONS

Seider, W. D., et al.; Product and Process Design Principles Synthesis, Analysis and Evaluation, Second Edition; pp. 231-299; vol. 7; John Wiley and Sons, Inc., 2004.

Duan, P., et al., Upgrading of Crude Algal Bio-Oil in Supercritical Water; Bioresource Technology; 2011; pp. 1899-1906; vol. 102; Elsevier Ltd.; www.elsevier.com/locate/biortech.

Peterson, A. A., et al., Thermochemical Biofuel Production in Hydrothermal Media: A Review of Sub- and Supercritical Water Technologies; Energy & Environmental Science; 2008; pp. 32-65; vol. 1; The Royal Society of Chemistry; www.rsc.org.ees.

Rudzinski, W. E., et al., A Review on Extraction and Identification of Crude Oil and Releated Products Using Supercritical Fluid Technology; Energy & Fuels; 2000; pp. 464-475; vol. 14; American Chemical Society.

* cited by examiner

PROCESS TO PRODUCE AROMATICS FROM CRUDE OIL

FIELD OF THE INVENTION

This invention relates to a method and apparatus for producing aromatics from crude oil. More specifically, the present invention relates to a method and apparatus for producing aromatics from a crude oil with supercritical water as the reaction medium.

BACKGROUND OF THE INVENTION

Crude oil serves as the dominant source of motor fuel and feedstock for the petrochemical industry. The quality, or economic value, of crude oil is determined based on the cleanliness and lightness of the crude. Cleanliness refers to having a low content of impurities, e.g., sulfurs, metals, asphaltenes. Lightness refers to the concentration of light and middle distillates. Middle distillate is generally defined as diesel-range hydrocarbons which have a boiling point between 175° C. and 370° C., depending on the specification of the diesel fuel of the country and refinery. Light distillate is generally defined as naptha-range hydrocarbons having lower boiling points than those of middle distillate. Upgrading processes are used to clean and lighten crude oil and other hydrocarbon streams, by subjecting those streams to various chemical reactions. There are a number of upgrading processes, many of which are designed for certain crude fractions, such as vacuum gas oil or vacuum residue.

Crude oil consists of a mixture of various types of molecules, including alkanes, alkenes, aromatics, and napthenes. Crude oil can be separated, based on boiling points, into gas, naptha, kerosene, diesel, vacuum gas oil (VGO), and vacuum residue (VR). A hydrocarbon solvent, such as n-heptane, can be used to separate crude oil into maltene and asphaltene. Asphaltene, primarily concentrated in vacuum residue, is most commonly thought to be a cluster of aromatic cores, linked by a non-aromatic network. The structure includes heteroatoms, such a sulfur, nitrogen, and oxygen and metals.

The precise compositions of crude oil or upgraded oil streams are unknowable due to the number of components present. Nor can composition be predicted based on the source of the crude oil or the nature of upgrading reactions. A crude oil from one source subjected to an upgrading reaction would have a product composition different from a crude oil from a second source subjected to the same upgrading reaction. Conversely, a crude oil subjected to an upgrading reaction aimed to desulfurize the stream would have a different composition if the same crude oil were subjected to a different desulfurization process. The inability to know the composition of the crude oil has led to the use of other measurements as ways to classify oil. One classification is boiling curve analysis, in which the temperature of a definitive volume percentage of a distillate fraction is measured. For example, a T95 is the temperature at which 95% of the distillate in a distillation column is vaporized. While T95 is a concept related to End Boiling Point (EBP), T95 provides a more representative value, because the presence of tiny amounts of large molecules can make EBP very high. The points, i.e., T95, can then be correlated to other industry developed property measures such as specific gravity, molecular weight, viscosity, and the API value.

Upgrading reactions can be used to preferentially generate certain components in the product. One such group of components that is targeted is aromatics. Aromatics are of increasing importance in industrial applications. For example, blending aromatics with gasoline results in a blended gasoline with a high octane rating.

Benzene, toluene, and xylene are three aromatics used in a variety of plastics, synthetic rubbers, and fibers. Collectively referred to as BTX, these aromatics can be preferentially produced by certain upgrading processes such as steam cracking or a fluidized catalytic cracking process or a reforming process. Most olefins, especially ethylene and propylene, are produced by such thermal processes.

In a steam cracking process, naptha is cracked to produce olefins, aromatics, and other hydrocarbons in the absence of a catalyst. The steam serves as a diluent, reducing the concentration of reactant and the generation of solid coke. Steam cracking processes can be designed to preferentially produce olefins. Steam cracking also can produce pyrolysis gasoline which can contain 70% by weight aromatics. Pyrolysis gasoline can be blended in the gasoline pool or subjected to further treatment. Steam cracking produces coke as a byproduct of the process.

Another thermal process is a fluidized catalytic cracking (FCC) process. In an FCC process, heavy hydrocarbons, such as vacuum gas oil and vacuum residue are converted to light hydrocarbons, including olefins, gasoline, and diesel. FCC processes are used in refineries to produce gasoline having a high octane rating and a light cycle oil (LCO) diesel fraction. Heavy cycle oil (HCO) is a blend for fuel oil, because the blend reduces the viscosity of the fuel oil. FCC processes use catalysts, which can be formulated to preferentially produce certain reaction products, but catalysts are expensive and suffer from deactivation, requiring reactivation in a separate regeneration unit to maintain productivity. Additionally, FCC units produce undesirable heavy products such as slurry oil and coke.

In a reforming process, straight run naptha is converted to a gasoline blendstock having a high octane rating due to an increased aromatic content. The aromatic content is increased using catalysts for dehydrocyclization, aromatization, cyclization, and dehydrogenation reactions in the presence of a large external supply of hydrogen. Reforming processes produce hydrogen in addition to hydrocarbon products. In general, the reformate product from a reforming process contains around 50 weight percent of aromatics. Like an FCC process, the catalyst in a reforming process is expensive and prone to deactivation by coking Coking can occur with slight fluctuations in the process or feedstock properties and conditions. Due to the expense of the catalyst, a regeneration unit is required to reactive spent catalyst.

Chemical reactions in the presence of supercritical water, such as supercritical water oxidation and supercritical water hydrolysis processes, are increasingly being explored. Supercritical water serves as a diluent, which reduces inter-radical reaction and the development of coke, and serves as a source of hydrogen. Thus, supercritical water shows promise as a reaction medium due to the ability to upgrade without the requirement of an external supply of hydrogen gas. Additionally, supercritical water can accelerate certain groups of reactions, such as cracking, which reduces reactor size. Supercritical water exhibits high selectivity which reduces coke generation.

Supercritical water is an alternate to the use of catalysts, because many catalysts are not stable under supercritical water conditions.

Upgrading reactions in the presence of supercritical water undergo radical chain reaction. It is expected that many of the above bonds crack immediately after being introduced to a supercritical water reactor due to the thermal energy present in the supercritical water. Carbon-heteroatom bonds, like carbon-sulfur bonds, including thiols and sulfides, carbon-nitrogen bonds, carbon-metal bonds, and weak carbon-carbon bonds are easily broken and generate radicals. The radicals of the broken bonds initiate the radical chain reaction. Radicals on molecules are propagated to other molecules which results in rearrangement of the molecular structure of the molecules to achieve cracking, oligomerization, isomerization, dehydrogenation, cyclization, aromatization, and other reactions. The order and nature of the products of upgrading reactions are sensitive to the operating conditions of the reactor and, therefore, are difficult to predict. Aromatic compounds, especially light aromatics such as benzene, toluene, and xylene (BTX) are self-inhibitors. That is, the delocalization of the radical by the aromatic structure causes a decrease in the concentration of radicals and an increase in the termination step.

The dominant source of BTX in supercritical water reactions is believed to be heavy aromatic compounds having a single aromatic core with an alkane chain. These heavy aromatic compounds are concentrated in asphaltene fractions, such as in vacuum residue. Dehydrocyclization of alkanes and dehydrogenation of napthenes also produce BTX, but in smaller quantities because of the complexity of the reaction network and the presence of competing reaction routes such as cracking.

Once a product stream rich in aromatics is produced, the BTX can be separated by distillation or by solvent extraction. Solvent extraction will not work for stream with low aromatic content, so in some cases concentrating the BTX between 20 vol % and 65 vol % is necessary prior to an extraction unit. Distillation takes advantage of the boiling point differences between hydrocarbon compounds, where the boiling point range of a naptha distillate is between 39° C. and 200° C. Solvent extraction, or liquid-liquid extraction, is a process whereby a solvent is used to separate a compound from a liquid based on its solubility in the solvent as compared to the solubility of the rest of the liquid.

SUMMARY

This invention relates to a method and apparatus for producing aromatics from crude oil. More specifically, the present invention relates to a method and apparatus for producing aromatics from a crude oil with supercritical water as the reaction medium.

In one aspect of the present invention, a process for producing aromatics from a hydrocarbon source in the presence of supercritical water is provided. The process includes the steps of mixing a pressurized, pre-heated water stream with a pressurized, pre-heated petroleum feedstock to create a combined stream, where the pressurized, pre-heated water stream and the pressurized, pre-heated petroleum feedstock are at a pressure above a critical pressure of water, where the pressurized, pre-heated water stream is heated to a temperature above a critical temperature of water, where the pressurized, pre-heated petroleum feedstock is heated to a temperature between 10° C. and 300° C., feeding the combined stream to a supercritical water reactor to create a modified stream, where the supercritical water reactor is in the absence of an external supply of hydrogen gas, where the supercritical water reactor is in the absence of catalyst, cooling the modified stream in a reactor cooler to create a cooled stream, where the cooled stream is cooled to a temperature below 200° C., depressurizing the cooled stream in a pressure reducer to create a depressurized stream, the depressurized stream includes water, aromatics, gases, and other hydrocarbons, wherein a pressure of the depressurized stream is between 0.05 MPa and 2.2 MPa, and separating the depressurized stream in a vapor-liquid separator to create a vapor stream and a liquid stream, the vapor stream including an amount of water, where the amount of water being water present in the depressurized stream. The method further includes the steps of condensing the vapor stream in a condenser to create a condensed stream, separating the condensed stream in a lights separator into a water recovery stream and a light product recovery stream, wherein the light product recovery stream contains the aromatics, and extracting the aromatics in an extraction unit from the light product recovery stream to create an aromatic extract stream and a light product stream. The method further includes the steps of depressurizing the liquid stream in a heavy pressure reducer to create a depressurized liquid stream, wherein a pressure of the depressurized stream is below 1 MPa, separating the depressurized liquid stream in a heavy separator into an upgraded product stream and a bottoms water stream, wherein the upgraded product stream includes an upgraded oil relative to the pressurized, pre-heated petroleum feedstock, and recycling part of the upgraded product stream to the pressurized, pre-heated petroleum feedstock as a product recycle.

In certain aspects of the present invention, the product recycle is split in a 1:1 ratio with a product stream. In certain aspects of the present invention, the supercritical water reactor is a two-stage reactor, the two-stage reactor including a first stage and a second stage, wherein a ratio of a residence time of the first stage to a residence time of the second stage is between 1.2:1 and 20:1. In certain aspects of the present invention, a temperature difference between the first stage and the second stage of the two-stage reactor is between 5° C. and 100° C. In certain aspects of the present invention, the first stage of the two-stage reactor is an upflow reactor. In certain aspects of the present invention, the second stage of the two-stage reactor is a downflow reactor. In certain aspects of the present invention, the aromatic extract stream includes benzene, toluene, and xylene. In certain aspects of the present invention, the modified stream has a higher content of aromatics and a lower content of impurities as compared to the pressurized, pre-heated petroleum feedstock. In certain aspects of the present invention, the amount of water in the vapor stream is greater than 90 wt % of the water present in the depressurized stream.

In a second aspect of the present invention, a process for producing aromatics from a hydrocarbon source in the presence of supercritical water is provided. The process including the steps of mixing a pressurized, pre-heated water stream with a pressurized, pre-heated petroleum feedstock to create a combined stream, where the pressurized, pre-heated water stream and the pressurized, pre-heated petroleum feedstock are at a pressure above the critical pressure of water, where the pressurized, pre-heated water stream is heated to a temperature above the critical temperature of water, where the pressurized, pre-heated petroleum feedstock is heated to a temperature between 10° C. and 300° C., feeding the combined stream to a supercritical water reactor to create a modified stream, where the supercritical water reactor is in the absence of an external supply of hydrogen gas, where the supercritical water reactor is in the absence of catalyst, cooling the modified stream in a reactor cooler to create a cooled stream, wherein the cooled stream is cooled to a temperature below 200° C., depressurizing the cooled stream in a pressure reducer to create a depressurized stream, the depressurized stream includes water and upgraded hydrocarbons, wherein a pressure of the depressurized stream is between 0.3 MPa and 2.2 MPa, and separating the depressurized stream in a vapor-liquid separator to generate a vapor stream and a liquid stream, wherein the liquid stream includes water and upgraded hydrocarbons. The process further includes the steps of separating the liquid stream in a heavy separator to produce a petroleum recovery stream and a water recovery stream, separating the petroleum recovery stream in a distillation column to produce a light product recovery stream and an upgraded product stream, where the light product recovery stream includes aromatics, and where the upgraded product stream includes upgraded hydrocarbons having a higher API gravity, lower sulfur content, and lower metal content compared to the pressurized, pre-heated petroleum feedstock, extracting the light product recovery stream in an extraction unit to produce a light product stream and an aromatic extract stream, mixing the light product stream with the upgraded product stream to create a mixed product stream, and recycling part of the mixed product stream to the pressurized, pre-heated petroleum feedstock as a product recycle.

In certain aspects of the present invention, the product recycle is split in a 1:1 ratio with a product stream. In certain aspects of the present invention, the supercritical water reactor is a two-stage reactor, the two-stage reactor including a first stage and a second stage, wherein a ratio of a residence time of the first stage to a residence time of the second stage is between 1.2:1 and 20:1. In certain aspects of the present invention, the temperature difference between the first stage and the second stage of the two-stage reactor is between 5° C. and 100° C. In certain aspects of the present invention, the first stage of the two-stage reactor is an upflow reactor. In certain aspects of the present invention, the second stage of the two-stage reactor is a downflow reactor. In certain aspects of the present invention, the aromatic extract stream includes benzene, toluene, and xylene. In certain aspects of the present invention, the modified stream has a higher content of aromatics and a lower content of impurities as compared to the pressurized, pre-heated petroleum feedstock. In certain aspects of the present invention, the amount of water in the vapor stream is greater than 90 wt % of the water present in the depressurized stream.

BRIEF DESCRIPTION OF THE DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended figures are set forth without any loss of generality, and without imposing limitations, relating to the claimed invention.

Figure 1:
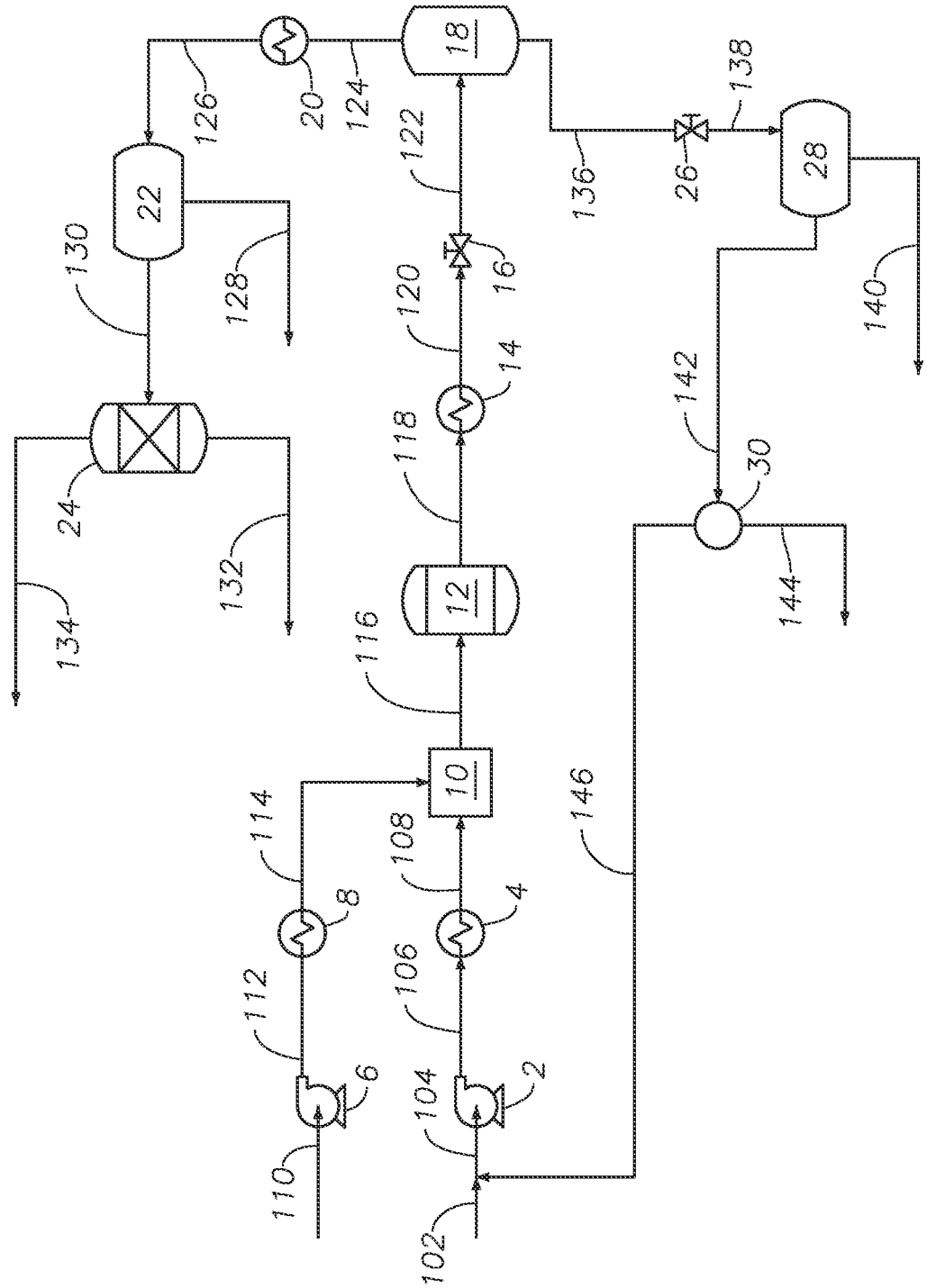
FIG. 1 provides a process diagram of one embodiment of the method of upgrading a hydrocarbon feedstock according to the present invention.
Figure 2:
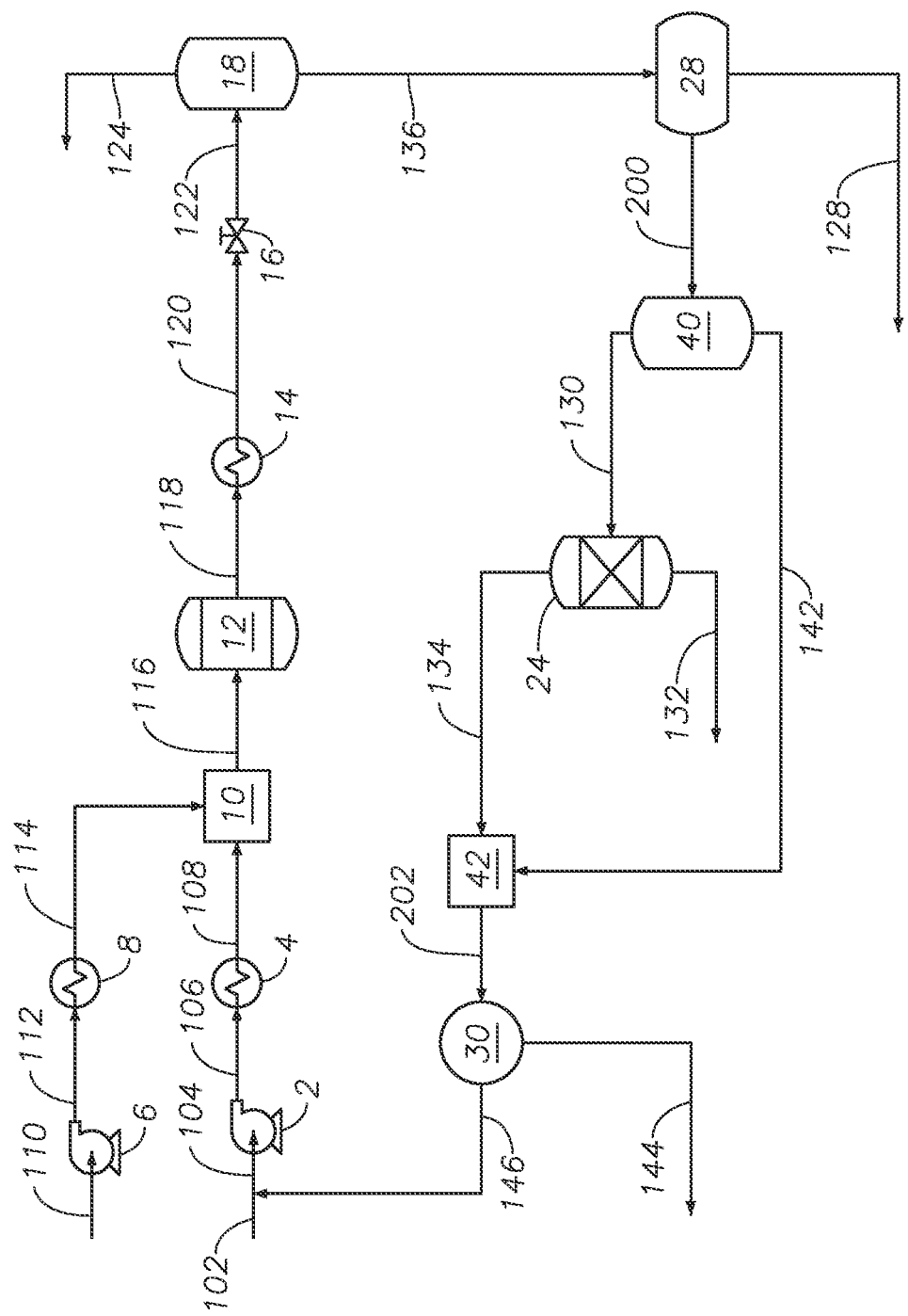
FIG. 2 provides a process diagram of a second embodiment of the method of upgrading a hydrocarbon feedstock according to the present invention.

Referring to FIGS. 1 and 2, embodiments of a process for producing aromatics from a hydrocarbon source in the presence of supercritical water are provided. Petroleum feedstock 102 is mixed with product recycle 146 to create mixed petroleum feedstock 104. Petroleum feedstock 102 can be from any hydrocarbon source. Exemplary hydrocarbon sources for petroleum feedstock 102 include whole range crude oil, distilled crude oil, residue oil, topped crude oil, product streams from oil refineries, product streams from steam cracking processes, liquefied coals, liquid products recovered from oil or tar sands, bitumen, oil shale, asphaltene, biomass hydrocarbons, and the like.

Mixed petroleum feedstock 104 is pressurized in petroleum feedstock pump 2 to create pressurized petroleum feedstock 106. The pressure of pressurized petroleum feedstock 106 is greater than about 22.064 MPa, alternately between about 22.1 MPa and about 31.9 MPa, alternately between about 22.9 MPa and about 31.1 MPa. In at least one embodiment of the present invention, the pressure of pressurized petroleum feedstock 106 is 25.0 MPa. The critical pressure of water is 22.064 MPa.

Pressurized petroleum feedstock 106 is heated in petroleum feedstock pre-heater 4 to form pre-heated petroleum feedstock 108. The temperature of pre-heated petroleum feedstock 108 is between about 10° C. and about 300° C., alternately between about 50° C. and 250° C., alternately between about 50° C. and 250° C., alternately between about 50° C. and 200° C., alternately between about 50° C. and 150° C., alternately between about 50° C. and about 100° C., alternately between about 100° C. and about 200° C., alternately between about 150° C. and about 250° C., alternately between about 200° C. and about 300° C. In at least one embodiment of the present invention, the temperature of pre-heated petroleum feedstock 108 is 60° C. Exemplary petroleum feedstock pre-heaters 4 include natural gas fired heater, heat exchanger, and electric heater. In some embodiments, pressurized petroleum feedstock 106 is heated in a cross-exchange operation with a heat exchanger later in the process.

Water stream 110 can be any source of water with a conductivity less than about 10.0 µmhos/cm. Exemplary water streams 110 include demineralized water, distilled water, boiler feed water, and deionized water. In at least one embodiment of the present invention, water stream 110 is a boiler feed water stream. Water stream 110 is pressurized in water pump 6 to produce pressurized water stream 112. The pressure of pressurized water stream 112 is greater than about 22.064 MPa, alternately between about 22.1 MPa and about 31.9 MPa, alternately between about 22.9 MPa and about 31.1 MPa. In at least one embodiment of the present invention, the pressure of pressurized water stream 112 is 25.0 MPa. The critical pressure of water is 22.064 MPa.

Pressurized water stream 112 is heated in water pre-heater 8 to create pre-heated water stream 114. The temperature of pre-heated water stream 114 is greater than about 374° C., alternately between about 374° C. and about 600° C., alternately between about 400° C. and about 550° C., alternately between about 400° C. and about 450° C., alternately between about 450° C. and about 500° C., alternately between about 500° C. and about 550° C., alternately between about 550° C. and about 600° C. In at least one embodiment of the present invention, the temperature of pre-heated water stream 114 is 520° C. The critical temperature of water is 373.946° C. Exemplary water pre-heaters 8 include a natural gas fired heater, a heat exchanger, and an electric heater. In some embodiments, pressurized water stream 112 is partially heated in a cross-exchange operation with a heat exchanger later in the process. In at least one embodiment of the present invention, pressurized water stream 112 is partially heated in a cross-exchange operation with modified stream 118. Pre-heated water stream 114 is supercritical water, water above the critical temperature and the critical pressure, or critical point. Above the critical temperature and pressure, the liquid and gas phase boundary of water disappears, and the fluid has characteristics of both fluid and gaseous substances. Supercritical water is able to dissolve organic compounds like an organic solvent and has excellent diffusibility like a gas. Regulation of the temperature and pressure allows for continuous "tuning" of the properties of the supercritical water to be more liquid or more gas like. Supercritical water has reduced density and lower polarity, as compared to liquid-phase sub-critical water, thereby greatly extending the possible range of chemistry which can be carried out in water. Supercritical water has various unexpected properties, and, as it reaches supercritical boundaries. Supercritical water has very high solubility toward organic compounds and has an infinite miscibility with gases. Furthermore, radical species can be stabilized by supercritical water through the cage effect (i.e., a condition whereby one or more water molecules surrounds the radical species, which then prevents the radical species from interacting). Stabilization of radical species is believed to help to prevent inter-radical condensation and thus, reduce the overall coke production in the current invention. For example, coke production can be the result of the inter-radical condensation. In certain embodiments, supercritical water generates hydrogen gas through a steam reforming reaction and water-gas shift reaction, which is then available for the upgrading reactions.

Pre-heated water stream 114 and pre-heated petroleum feedstock 108 are mixed in feed mixer 10 to produce combined stream 116. Feed mixer 10 can be any type of mixing device capable of mixing pre-heated water stream 114 and pre-heated petroleum feedstock 108. In at least one embodiment of the present invention, feed mixer 10 is an inline mixer. Combined stream 116 has a ratio of water to hydrocarbons represented by a ratio of the volumetric flow rate of water stream 110 ($v_{110}$) to the volumetric flow rate of petroleum feedstock 102 ($v_{102}$). The ratio of $v_{110}$ to $v_{102}$ is in the range from about 10:1 to about 1:10, alternately about 5:1 to about 1:5, alternately less than 4:1, alternately less than 3:1, and alternately less than 2:1. In at least one embodiment of the present invention, the ratio of $v_{110}$ to $v_{112}$ is 1.4/1. In at least one embodiment of the present invention, the ratio of $v_{110}$ to $v_{112}$ is 2.5/1. Combined stream 116 is fed to reactor 12.

Reactor 12 is a supercritical water reactor, employing supercritical water as the reaction medium for upgrading reactions in the absence of externally-provided hydrogen gas and in the absence of a catalyst. The reaction products in modified stream 118 are attributable to the composition of petroleum feedstock 102, the ratio of ratio of $v_{110}$ to $v_{102}$, and the operating temperature of reactor 12.

The operating temperature of reactor 12 affects the presence of aromatic radicals capable of radical inhibition of upgrading reactions. Supercritical water increases the likelihood that upgrading reactions produce BTX. BTX inhibits upgrading reactions by capturing radicals and preventing radical chain reactions. The production of BTX increases with increasing temperature. The propensity for BTX to act as an inhibitor decreases with increasing temperature. Temperature plays an important role in the exact product mix from reactor 12.

Temperature also affects the production of coke in reactor 12. Coking is an undesirable by-product of upgrading reactions. Increasing temperature increases coke production. One way to reduce coking is to ensure mixing of hydrocarbon, especially asphaltene portion, with supercritical water. Pressure impacts the density of water. At 25 MPa, the density of water at 400° C. is 166.54 kg/m$^3$ while at 450° C. the density is 108.98 kg/m$^3$. This density change may impact the mixing ability of supercritical water and hydrocarbons. A second way to reduce coking is to ensure a sufficient amount of diluent is present in the reaction mixture. Aromatics and BTX act as a diluent when present. In at least one embodiment of the present invention, combined stream 116 is in the absence of quantities of BTX or aromatics to act as a diluent. In at least one embodiment of the present invention, supercritical water acts as a diluent in reactor 12.

Reactor 12 can be a single-stage, two-stage, or three-stage reactor. In multi-stage reactors, such as two-stage or three-stage reactors, the effluent stream from a first stage is the feed stream to the second stage. The operating temperature of each stage of reactor 12 is greater than about 374° C., alternately between about 374° C. and about 600° C., alternately between about 380° C. and about 420° C., alternately between about 390° C. and about 450° C., alternately between 400° C. and about 550° C., alternately between about 400° C. and about 450° C., alternately between 450° C. and about 500° C., alternately between about 500° C. and about 550° C., alternately between about 550° C. and about 600° C.

The residence time of each stage of reactor 12 is between about 1 second and about 120 minutes, alternately between about 30 seconds and about 20 minutes, alternately between 1 minute and about 10 minutes, alternately between about 5 minutes and about 15 minutes, alternately between about 8 minutes and about 12 minutes, alternately between about 10 minutes and about 20 minutes, alternately between about 20 minutes and about 30 minutes, alternately between about 30 minutes and about 40 minutes, alternately between about 40 minutes and 50 minutes, alternately between about 50 minutes and 60 minutes, alternately between about 60 minutes and 90 minutes, alternately between about 60 minutes and 120 minutes. The flow direction of each stage of reactor 12 can be upflow or downflow.

In at least one embodiment of the present invention, reactor 12 is single-stage reactor with an operating temperature of 400° C., a residence time of 10 minutes, and an upflow flow direction.

In multi-stage reactors, the ratio of residence time of a first stage to a subsequent stage is such that the residence time in the first stage is longer than the residence time in any subsequent stage. The ratio of residence time of a first stage to a subsequent stage is between about 1.2:1 and about 20:1, alternately between about 2:1 and about 10:1, alternately between about 2:1 and about 6:1. In a preferred embodiment, reactor 12 is a two-stage reactor where each stage has a different operating temperature and a different residence time. In a two-stage reactor, the temperature difference between the first stage and the second stage of reactor 12 is between about 5° C. and about 100° C., alternately between about 10° C. and about 50° C., alternately between about 20° C. and about 40° C. In at least one embodiment of the present invention, the temperature difference between the first stage of reactor 12 and the second stage of reactor 12 is 30° C.

In at least one embodiment of the present invention, reactor 12 is a two-stage reactor with a longer residence time in the first stage compared to the second stage. The first stage of reactor 12 provides mixing of combined stream 116 at a temperature lower than 420° C. The upgrading reactions begin at entry to the first stage, but the coking is minimized. The second stage of reactor 12 is at a temperature above 420° C., the increased temperature increases the production of BTX while reducing the inhibition caused by BTX. With respect to BTX production, the use of two stages balances BTX production and BTX inhibition. The shorter residence time in the second stage minimizes coking production.

In a preferred embodiment of the present invention, reactor 12 is a two-stage reactor, where the first stage has an operating temperature of 400° C. and an upflow flow direction, the second stage has an operating temperature of 430° C. and a downflow flow direction, and the ratio of the residence time of the first stage to the second stage is 4:1.

Reactor 12 outlet is modified stream 118. Modified stream 118 is cooled in reactor cooler 14 to create cooled stream 120. Cooled stream 120 has a temperature between about 10° C. and about 200° C., alternately between about 30° C. and about 120° C., alternately between about 50° C. and about 100° C. In at least one embodiment of the present invention, the temperature of cooled stream 120 is 60° C. Exemplary reactor coolers 14 include a heat exchanger, a steam generator, or a cross-exchanger. In at least one embodiment of the present invention, reactor cooler 14 is a cross-exchanger that heats pressurized water stream 112 with heat from modified stream 118. One of skill in the art will appreciate that cross-exchange heat exchangers can be utilized to provide energy recovery within the system.

The pressure of cooled stream 120 is reduced in pressure reducer 16 to form depressurized stream 122. The pressure of depressurized stream 122 is between about 0 MPa and about 2.2 MPa, alternately between about 0.05 MPa and about 1.2 MPa, alternately between about 0.05 MPa and about 1.0 MPa, alternately between about 0.1 MPa and about 0.5 MPa. In at least one embodiment of the present invention, the pressure of depressurized stream 122 is 0.1 MPa. Pressure reducer 16 can be any type of depressurizing device capable of reducing the pressure of cooled stream 120. Exemplary devices suitable for use pressure reducer 16 include pressure control valve and capillary-type pressure let-down device.

Modified stream 118, cooled stream 120, and depressurized stream 122 contain water, aromatics (BTX), and other hydrocarbons. Depressurized stream 122 further includes gases, such as carbon dioxide. Modified stream 118, cooled stream 120, and depressurized stream 122 have a higher content of aromatics and a lower content of impurities as compared to petroleum feedstock 102. The boiling point range of hydrocarbons in depressurized stream 122 is lower compared than the boiling range of hydrocarbon present in petroleum feedstock 102. The mass fraction of water present in modified stream 118, cooled stream 120, and depressurized stream 122 depends on the operating conditions in reactor 12, the flow rate of water stream 110 and the feed ratio of water to hydrocarbon in combined stream 116. Depressurized stream 122 is fed to vapor-liquid separator 18.

Vapor-liquid separator 18 separates depressurized stream 122 into vapor stream 124 and liquid stream 136. Vapor-liquid separator 18 is a gas-liquid separator. Exemplary separators useful for vapor-liquid separator 18 include flash drum, flash column, multi-stage column, stripping-type column.

The operating conditions of reactor cooler 14, pressure reducer 16, and vapor-liquid separator 18 are adjusted in consideration of the processing steps performed on vapor stream 124 and liquid stream 136. The operating conditions of reactor cooler 14, pressure reducer 16, and vapor-liquid separator 18 effect the total amount and the compositions in vapor stream 124 and liquid stream 136.

Referring to FIG. 1, an embodiment of the present invention with additional processing steps for vapor stream 124 is provided. Vapor stream 124 contains an amount of water, the amount of water being water present in depressurized stream 122. The amount of water present in vapor stream 124 is greater than about 90 wt % of the water present in depressurized stream 122, alternately greater than about 92 wt % of the water present in depressurized stream 122, alternately greater than about 95 wt % of the water present in depressurized stream 122, alternately greater than about 97 wt % of the water present in depressurized stream 122, alternately greater than about 99% of the water present in depressurized stream 122. The operating conditions of vapor-liquid separator 18 are controlled to adjust the amount of water present in vapor stream 124. In at least one embodiment of the present invention, the pressure of depressurized stream 122 is 96 psig (0.662 MPa) and the temperature of vapor-liquid separator 18 is 167° C. and the amount of water present in vapor stream 124 is greater than 95 wt % of the water present in depressurized stream 122. The mass fraction of water present in vapor stream 124 also depends on the flow rate of water stream 110 and the feed ratio of water to hydrocarbon in combined stream 116 to reactor 12.

Vapor stream 124 contains the BTX present in depressurized stream 122 along with other light hydrocarbons. As used herein light hydrocarbons is defined as hydrocarbons having boiling points below 320° C., alternately less than 280° C. In at least one embodiment of the present invention, vapor stream 124 has a higher concentration of BTX than depressurized stream 122.

Vapor stream 124 is cooled in condenser 20 to produce condensed stream 126. Condensed stream 126 is fed to lights separator 22, which separates condensed stream 126 into hydrocarbons in light product recovery stream 130, and water in water recovery stream 128. Without being bound to a particular theory, the absence of heavy hydrocarbons in condensed stream 126 facilitates the separation of hydrocarbons and water in lights separator 22.

Water recovery stream 128 can be recycled to the front of the process, can be used in a different process unit, can be treated for further use, can be treated for disposal, or can be stored.

Light product recovery stream 130 is fed to solvent extraction unit 24. Light product recovery stream 130 contains at least about 1.0% by volume BTX, alternately at least about 0.5% by volume BTX, and alternately at least about 0.1% by volume BTX. Solvent extraction unit 24 separates light product recovery stream 130 into aromatic extract stream 132 and light product stream 134. In at least one embodiment of the present invention, light product recovery stream 130 is fed to a distillation unit upstream of solvent extraction unit 24 to increase the concentration of BTX in the stream fed to solvent extraction unit 24. In at least one embodiment of the present invention, the process is in the absence of a distillation column because fractionation occurs in vapor-liquid separator 18. In at least one embodiment of the present invention, aromatic extract stream 132 is sent to a processing unit to further purify the BTX. The processing unit to purify the BTX can be used for any method known to one of skill in the art for processing BTX. In at least one embodiment of the present invention, light product stream 134 is blended with other upgraded hydrocarbon streams.

Liquid stream 136 is depressurized in heavy pressure reducer 26 to create depressurized liquid stream 138. Depressurized liquid stream 138 is at a pressure of less than about 1.0 MPa and preferably less than about 0.1 MPa. Depressurized liquid stream 138 is fed to heavy separator 28 to separate depressurized liquid stream 138 into hydrocarbons in upgraded product stream 142 and water in bottoms water stream 140.

Bottoms water stream 140 can be recycled to the front of the process, can be used in a different process unit, can be treated for further use, can be treated for disposal, or can be stored. Bottoms water stream 140 can be combined with water recovery stream 128 prior to the next stage.

Upgraded product stream 142 is separated into multiple streams in recycle tee 30. Upgraded product stream 142 has a lower total content of asphaltene, metals, sulfur, and nitrogen compared to petroleum feedstock 102. In at least one embodiment of the present invention, upgraded product stream 142 has a higher concentration of impurities than petroleum feedstock 102.

Product recycle 146 is recycled to the beginning of the process to be mixed with petroleum feedstock 102. Product recycle 146 contains unconverted hydrocarbons present in petroleum feedstock 102. In at least one embodiment of the present invention, product recycle 146 contains upgraded hydrocarbons. In at least one embodiment of the present invention, product recycle 146 is heavier than naptha. In at least one embodiment of the present invention, product recycle 146 contains fewer aromatics, including BTX, than petroleum feedstock 102. In at least one embodiment of the present invention, product recycle 146 is in the absence of aromatics, including BTX, than petroleum feedstock 102. Product stream 144 can be processed further, can be sent to an upgraded oil pool, or can be treated for transfer offsite.

Referring to FIG. 2, in at least one embodiment of the present invention, vapor stream 124 is not subjected to further processing to recover hydrocarbons. Vapor stream 124 can be treated for disposal or treated to recover water.

Liquid stream 136 is fed to heavy separator 28, which separates liquid stream 136 into petroleum recovery stream 200 and water recovery stream 128. Heavy separator 28 is any type of oil-water separator capable of separating hydrocarbons present in liquid stream 136 from water. Heavy separator 28 can be a two-phase or a three-phase separator. In at least one embodiment of the present invention, heavy separator 28 is a three-phase vapor-oil-water separator. Exemplary oil-water separators suitable for use as heavy separator 28 include multi-stage settling vessel, gravity separation, and coalescer. Petroleum recovery stream 200 has higher API gravity, lower sulfur content, lower metal content, and higher light and middle distillate fraction than petroleum feedstock 102. Water recovery stream 128 is treated as described with reference to FIG. 1.

Petroleum recovery stream 200 is fed to distillation column 40. Distillation column 40 separates petroleum recovery stream 200 to produce light product recovery stream 130 and upgraded product stream 142. Distillation column 40 is adjusted to achieve a light product recovery stream 130 with T95 between about 150° C. and about 300° C., alternately between about 180° C. and about 220° C. In a preferred embodiment of the present invention, the T95 is 200° C. Upgraded product stream 142 has a higher API gravity, lower sulfur content, and lower metal content compared to petroleum feedstock 102.

Light product recovery stream 130 is fed to solvent extraction unit 24. Solvent extraction unit 24 separates light product recovery stream 130 into light product stream 134 and aromatic extract stream 132. Solvent extraction unit 24 can be any commercially available extraction unit or process that will separate benzene, toluene, and xylene (BTX) from a process stream. In an alternate embodiment of the present invention, solvent extraction unit 24 can be an alternate type of BTX separation, such as azeotropic distillation, adsorption, and extractive distillation. In at least one embodiment of the present invention, aromatic extract stream 132 is fed to a BTX fractionation unit to recover the solvent used in solvent extraction unit 24.

Light product stream 134 and upgraded product stream 142 are mixed in product mixer 42 to produce mixed product stream 202. Mixed product stream 202 is separated at recycle tee 30 into product recycle 146 and product stream 144. Product recycle 146 is fed to the beginning of the process to be mixed with petroleum feedstock 102. Product recycle 146 contains unconverted hydrocarbons present in petroleum feedstock 102. In at least one embodiment of the present invention, product recycle 146 contains upgraded hydrocarbons. In at least one embodiment of the present invention, product recycle 146 is heavier than naptha. In at least one embodiment of the present invention, product recycle 146 contains fewer aromatics, including BTX, than petroleum feedstock 102. In at least one embodiment of the present invention, product recycle 146 is in the absence of aromatics, including BTX, than petroleum feedstock 102. Product stream 144 is an upgraded oil stream relative to petroleum feedstock 102. Product stream 144 has a lower total content of asphaltene, metals, sulfur, and nitrogen compared to petroleum feedstock 102. In at least one embodiment of the present invention, product stream 144 has a higher concentration of impurities than petroleum feedstock 102. Product stream 144 can be fed to a refinery or to other processing units.

In certain embodiments, the present invention provides a method for upgrading a hydrocarbon source, e.g. petroleum feedstock 102, utilizing supercritical water, by a process which specifically excludes the use of an external supply of hydrogen gas, and also specifically excludes the use of catalyst for the reaction. The upgrading reactions result in upgraded hydrocarbon product having an increased production of aromatics, reduced coke production, and/or significant removal of impurities, such as, compounds containing sulfur, nitrogen and metals. In general, the use of hydrogen gas is avoided for use with the hydrothermal process due to economic and safety concerns. In addition, the methods described herein result in various other improvements in the petroleum product, including higher API gravity, higher light distillate yield, higher middle distillate yield (as compared with the middle distillate present in both the feedstock and comparable upgrading processes), and hydrogenation of unsaturated compounds present in petroleum feedstock 102.

EXAMPLES

Example 1

Figure 3:
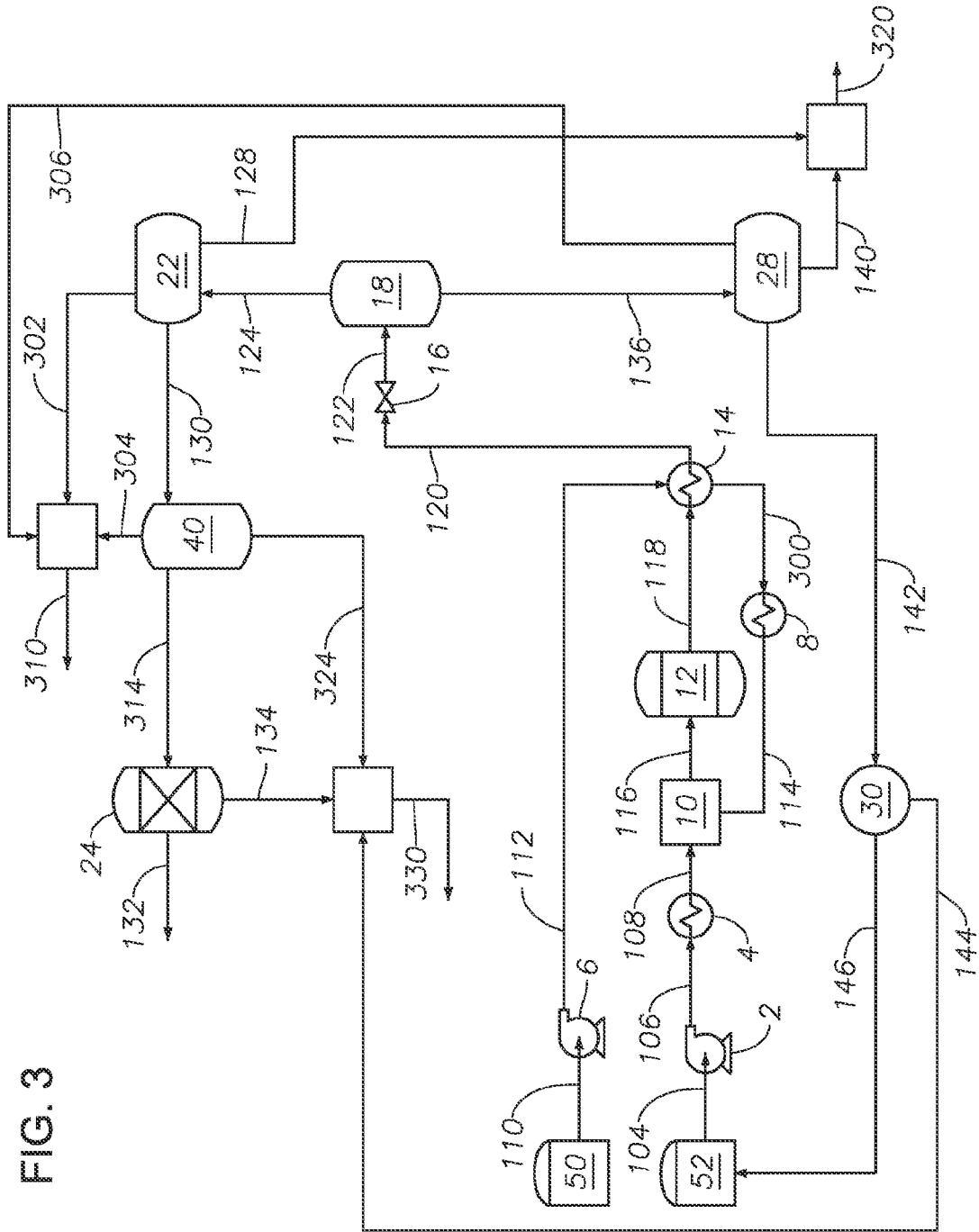
FIG. 3 provides a process diagram of the model used to simulate a process of the present invention.

Example 1 provides a simulated model of an embodiment of the present invention as described with reference to FIG. 3. The simulation modeled a whole range Arabian heavy crude oil hydrocarbon source, as mixed petroleum feedstock 104 from petroleum storage 52 at a volumetric flow rate of 20,000 barrels/day was pressurized to a pressure of 3611 psig (24.9 MPa) in petroleum feedstock pump 2 to create pressurized petroleum feedstock 106. Pressurized petroleum feedstock 106 was pre-heated to a temperature of 50° C. in petroleum feedstock pre-heater 4 to create pre-heated petroleum feedstock 108. Water stream 110 from water storage 50 at a volumetric flow rate of 20,000 barrels/day was pressurized to a pressure of 3611 psig (24.9 MPa) in water pump 6 to create pressurized water stream 112. Pressurized water stream 112 was pre-heated first in a cross exchanger operation with modified stream 118, in reactor cooler 14 to create heated water stream 300. Heated water stream 300 was heated further in water pre-heater 8 to create pre-heated water stream 114. Pre-heated petroleum feedstock 108 and pre-heated water stream 114 were mixed in feed mixer 10 to form combined stream 116. The outlet temperature from water pre-heater 8 was controlled such that combined stream 116 was at a temperature of 368° C. Combined stream 116 was fed to reactor 12, a supercritical water reactor. Reactor 12 employed two reaction zones in series. The first reaction zone had an internal temperature of 400° C. and a residence time of 4 minutes. The second reaction zone had an internal temperature of 430° C. and a residence time of 1 minute. Reactor 12 effluent, or modified stream 118, was cooled to 220° C. through reactor cooler 14, with a pressure drop of 611 psig (4.21 MPa). The pressure in cooled stream 120 was reduced further in pressure reducer 16, simulated as a pressure control valve, to 96 psig (0.662 MPa). Depressurized stream 122 was separated in vapor-liquid separator 18, a flash drum, generating vapor stream 124 and liquid stream 136. Both streams were further separated in three-phase separators: lights separator 22 and heavy separator 28. Light product recovery stream 130 from lights separator 22 was fed to distillation column 40. Demulsifier was added to heavy separator 28 to accelerate the separation of oil and water, which was necessary because of the presence of heavy components, such as asphaltene. Product draw 314 was pulled off from distillation column 40 and subjected to a solvent extraction process in solvent extraction unit 24. The total process produced four product streams: recovered upgraded product stream 330, recovered vapor 310, recovered water 320, and aromatic extract stream 132. Upgraded product stream 142, the oil fraction from heavy separator 28 was partially recycled, through recycle tee 30, to petroleum storage 52 to be mixed with the whole crude oil as product recycle 146. Recovered upgraded product stream 330 was a mix of bottoms product stream 324 from distillation column 40, light product stream 134, the raffinate stream from solvent extraction unit 24, and product stream 144, the portion of upgraded product stream 142 not recycled. Recovered vapor 310 was a mix of overhead vapor 304 from distillation column 40, lights vapor stream 302 from lights separator 22, and heavy vapor stream 306 from heavy separator 28. Recovered water 320 was a mix of water recovery stream 128 from lights separator 22 and bottoms water stream 140 from heavy separator 28. Finally, aromatic extract stream 132 from the solvent extraction process of solvent extraction unit 24 contained most of the benzene, toluene, and xylene (BTX) produced in the reaction zones of reactor 12. Table 1 shows selected stream properties. Table 2 shows additional properties of selected streams. Table 3 shows selected components of selected streams.

The results indicate that vapor stream 124 from vapor-liquid separator 18 contained 95% of the water present in modified stream 118. The distillation point up to 95 vol % (T95%) of the hydrocarbon fractions contained in vapor stream 124 was 252° C. measured by the ASTM D86 method. The distillation point up to 5 vol % (T5%) of the hydrocarbon fractions contained in liquid stream 136 is 256° C. measured by the ASTM D86 method. These results indicate that vapor stream 124 has light hydrocarbons only. The absence of heavy molecules makes the oil-water separation simpler. The results also show that about 92 wt % of toluene in modified stream 118 is in light product recovery stream 130 from lights separator 22, resulting in a concentration of 44 wt % toluene in product draw 314 from distillation column 40. Product recycle 146 is heavier than naptha.

TABLE 1

| | | | | | | | | | |
|---|---|---|---|---|---|---|---|---|---|
| Conditions of Streams | | | | | | | | | |
| Stream Property | 102 | 104 | 108 | 110 | 112 | 300 | 114 | 116 | 118 |
| Temperature (° C.) | 16 | 22 | 50 | 20 | 22 | 370 | 425 | 368 | 450 |
| Pressure (psig) | 1 | 3611 | 3611 | 1 | 3611 | 3611 | 3611 | 3611 | 3611 |
| Mass Flow (kg/h) | 117966 | 117966 | 117966 | 132223 | 132223 | 132223 | 132223 | 250189 | 250189 |
| Liquid Volume Flow (barrel/day) | 20000 | 20000 | 20000 | 20000 | 20000 | 20000 | 20000 | 40000 | 40820 |
| Mass Flow $H_2O$ (kg/h) | 0 | 0 | 0 | 132223 | 132223 | 132223 | 132223 | 132223 | 132223 |
| Mass Flow Toluene (kg/h) | 381 | 381 | 381 | 0 | 0 | 0 | 0 | 381 | 991 |
| Stream Property | 120 | 122 | 124 | 136 | 302 | 130 | 128 | 304 | 324 |
| Temperature (° C.) | 230 | 164 | 167 | 167 | 60 | 60 | 60 | 8 | 191 |
| Pressure (psig) | 3000 | 96 | 96 | 96 | 96 | 96 | 96 | 1 | 2 |
| Mass Flow (kg/h) | 250189 | 250189 | 155564 | 94625 | 2443 | 20861 | 132260 | 999 | 14167 |
| Liquid Volume Flow (barrel/day) | 40820 | 40820 | 24962 | 15858 | 785 | 4157 | 20019 | 276 | 2704 |
| Mass Flow $H_2O$ (kg/h) | 132223 | 132223 | 131974 | 249 | 41 | 8 | 131925 | 7 | 0 |
| Mass Flow Toluene (kg/h) | 991 | 991 | 928 | 63 | 15 | 913 | 0 | 0 | 0 |
| Stream Property | 142 | 144 | 310 | 314 | 146 | 330 | 320 | 132 | 134 |
| Temperature (° C.) | 167 | 167 | 41 | 119 | 167 | 157 | 60 | 123 | 10 |
| Pressure (psig) | 96 | 96 | 1 | 1 | 96 | 1 | 96 | 1 | 1 |

TABLE 1-continued

Conditions of Streams

| Mass Flow (kg/h) | 94625 | 47313 | 3442 | 2959 | 47313 | 65808 | 132260 | 1366 | 1593 |
|---|---|---|---|---|---|---|---|---|---|
| Liquid Volume Flow (barrel/day) | 15858 | 7929 | 1061 | 548 | 7929 | 11574 | 20019 | 237 | 311 |
| Mass Flow H$_2$O (kg/h) | 249 | 124 | 49 | 0 | 124 | 125 | 131925 | 0 | 0 |
| Mass Flow Toluene (kg/h) | 63 | 31 | 15 | 913 | 31 | 31 | 0 | 913 | 0 |

TABLE 2

Representative Properties of Selected Streams

| | Stream 102 | Stream 330 | Stream 146 |
|---|---|---|---|
| Mass Flow (kg/hr) | 117966 | 65686 | 47190 |
| Relative Mass Flow | 100% | 56% | 40% |
| API Gravity | 27 | 33 | 25 |
| TBP 5% (° C.) | 59 | 67 | 210 |
| TBP 10% (° C.) | 99 | 155 | 239 |
| TBP 30% (° C.) | 228 | 220 | 332 |
| TBP 50% (° C.) | 361 | 313 | 424 |
| TBP 70% (° C.) | 501 | 438 | 516 |
| TBP 90% (° C.) | 695 | 601 | 648 |
| TBP 95% (° C.) | 777 | 651 | 684 |

TABLE 3

Selected Components of Selected Streams

| Mass flow (kg/hr) | Stream 102 | Stream 122 | Stream 132 |
|---|---|---|---|
| Benzene | 46 | 69 | 10 |
| Toluene | 381 | 991 | 913 |
| p-Xylene | 74 | 109 | 92 |
| m-Xylene | 163 | 245 | 207 |
| o-Xylene | 130 | 188 | 145 |

Example 2

Comparative Example

Example 2 used the same simulated model and inputs as Example 1, with one notable difference. The set-up of reactor 12 was different in Example 2, specifically the second reaction zone had an internal temperature of 400° C. and a residence time of 1 minute. Table 4 shows selected components of selected streams.

Table 5 suggests that the content of benzene, toluene, and xylene in stream 132 is sensitive to the operating conditions of reactor 12.

TABLE 4

Comparative Example of Selected Components of Selected Streams

| Mass flow (kg/hr) | Stream 102 | Stream 122 | Stream 132 |
|---|---|---|---|
| Benzene | 46 | 49 | 2 |
| Toluene | 381 | 661 | 603 |
| p-Xylene | 74 | 91 | 78 |
| m-Xylene | 163 | 189 | 163 |
| o-Xylene | 130 | 145 | 120 |

TABLE 5

Comparison of the Aromatic Extract Stream

| Mass flow (kg/hr) | Example 1 | Example 2 |
|---|---|---|
| Benzene | 10 | 2 |
| Toluene | 913 | 603 |
| p-Xylene | 92 | 78 |
| m-Xylene | 207 | 163 |
| o-Xylene | 145 | 120 |
| Total BTX of 1000 | 1367 | 966 |

Example 3

Deionized water and whole range Arabian Heavy crude oil (API gravity at 60° F.=26.5°) were pumped by independent metering pumps at the rate of 0.96 liter/hr and 0.62 liter/hr, respectively. Pressurized water and crude oil were pre-heated by independent electric heaters to reach at 513° C. and 50° C., respectively. Two pre-heated streams were combined by a tee fitting. The first reactor had 1 liter internal volume and impeller-type agitator to enhance mixing of water and oil. The second reactor had 0.25 liter internal volume and impeller-type agitator too. The temperatures of the reactors were set to 400° C. and 430° C. for the first and second reactors, respectively. Reactor effluent was cooled down by double pipe type heat exchanger to be lower than 50° C. Stream was depressurized by back pressure regulator to atmospheric pressure. Product was separated into water and oil by using centrifuge machine and oil product was analyzed by distillation and gas chromatography. The amounts of toluene included in the feed crude oil and product oil were 0.33 wt % and 0.86 wt %. Increase of toluene amount was about 2.6 times.

Example 4

As a comparative example, reactor temperatures were set to 400° C. Other operating conditions were same. In this case, the amounts of toluene included in the feed crude oil and product oil were 0.33 wt % and 0.65 wt %. Increase of toluene amount was about 2.0 times.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

That which is claimed is:

1. A process for producing aromatics from a hydrocarbon source in the presence of supercritical water, the process comprising the steps of:
   mixing a pressurized, pre-heated water stream with a pressurized, pre-heated petroleum feedstock to create a combined stream,
      wherein the pressurized, pre-heated water stream and the pressurized, pre-heated petroleum feedstock are at a pressure above a critical pressure of water,
      wherein the pressurized, pre-heated water stream is heated to a temperature above a critical temperature of water,
      wherein the pressurized, pre-heated petroleum feedstock is heated to a temperature between 10° C. and 300° C.;
   feeding the combined stream to a supercritical water reactor to produce a modified stream comprising water, aromatics and other hydrocarbons, wherein the supercritical water reactor is operated in an absence of an external supply of hydrogen gas and wherein the supercritical water reactor is operated in an absence of catalyst;
   cooling the modified stream in a reactor cooler to create a cooled stream, wherein the cooled stream is cooled to a temperature below 200° C.;
   depressurizing the cooled stream in a pressure reducer to create a depressurized stream, the depressurized stream comprising water, aromatics, gases, and other hydrocarbons, wherein a pressure of the depressurized stream is between 0.05 MPa and 2.2 MPa;
   separating the depressurized stream in a vapor-liquid separator to create a vapor stream and a liquid stream, the vapor stream comprising an amount of water and aromatics comprising benzene, toluene, and xylene, wherein the amount of water being a portion of the water present in the depressurized stream;
   condensing the vapor stream in a condenser to create a condensed stream;
   separating the condensed stream in a lights separator into a water recovery stream and a light product recovery stream, wherein the light product recovery stream contains the aromatics;
   extracting the aromatics in an extraction unit from the light product recovery stream to create an aromatic extract stream comprising benzene, toluene, and xylene, and a light product stream
   depressurizing the liquid stream in a heavy pressure reducer to create a depressurized liquid stream, wherein a pressure of the depressurized liquid stream is below 1 MPa;
   separating the depressurized liquid stream in a heavy separator into an upgraded product stream and a bottoms water stream, wherein the upgraded product stream comprises upgraded hydrocarbons relative to the pressurized, pre-heated petroleum feedstock; and
   recycling part of the upgraded product stream to the pressurized, pre-heated petroleum feedstock as a product recycle.

2. The process of claim 1, wherein the product recycle is split in a 1:1 ratio with a product stream.

3. The process of claim 1, wherein the supercritical water reactor is a two-stage reactor, the two-stage reactor comprising a first stage and a second stage, wherein a ratio of a residence time of the first stage to a residence time of the second stage is between 1.2:1 and 20:1.

4. The process of claim 3, wherein a temperature difference between the first stage and the second stage of the two-stage reactor is between 5° C. and 100° C.

5. The process of claim 3, wherein the first stage of the two-stage reactor is an upflow reactor and wherein the second stage of the two-stage reactor is a downflow reactor.

6. The process of claim 1, wherein the modified stream has a higher content of aromatics and a lower content of impurities as compared to the pressurized, pre-heated petroleum feedstock.

7. The process of claim 1, wherein the amount of water in the vapor stream is greater than 90 wt % of the water present in the depressurized stream.

8. A process for producing aromatics from a hydrocarbon source in the presence of supercritical water, the process comprising the steps of:
   mixing a pressurized, pre-heated water stream with a pressurized, pre-heated petroleum feedstock to create a combined stream,
      wherein the pressurized, pre-heated water stream and the pressurized, pre-heated petroleum feedstock are at a pressure above a critical pressure of water,
      wherein the pressurized, pre-heated water stream is heated to a temperature above a critical temperature of water,
      wherein the pressurized, pre-heated petroleum feedstock is heated to a temperature between 10° C. and 300° C.;
   feeding the combined stream to a supercritical water reactor to produce a modified stream comprising water, aromatics and upgraded hydrocarbons, wherein the supercritical water reactor is operated in an absence of an external supply of hydrogen gas and wherein the supercritical water reactor is operated in an absence of catalyst;
   cooling the modified stream in a reactor cooler to create a cooled stream, wherein the cooled stream is cooled to a temperature below 200° C.;
   depressurizing the cooled stream in a pressure reducer to create a depressurized stream, the depressurized stream comprising water, aromatics comprising benzene, toluene, and xylene, and upgraded hydrocarbons, wherein a pressure of the depressurized stream is between 0.3 MPa and 2.2 MPa;
   separating the depressurized stream in a vapor-liquid separator to generate a vapor stream and a liquid stream, wherein the liquid stream comprises the water, the aromatics, and the upgraded hydrocarbons;
   separating the liquid stream in a heavy separator to produce a petroleum recovery stream comprising the aromatics and upgraded hydrocarbons, and a water recovery stream;

separating the petroleum recovery stream in a distillation column to produce a light product recovery stream and an upgraded product stream,
  wherein the light product recovery stream comprises the aromatics, and
  wherein the upgraded product stream comprises the upgraded hydrocarbons, the upgraded product stream having a higher API gravity, lower sulfur content, and lower metal content compared to the pressurized, pre-heated petroleum feedstock;
extracting the light product recovery stream in an extraction unit to produce a light product stream and an aromatic extract stream comprising benzene, toluene, and xylene;
mixing the light product stream with the upgraded product stream to create a mixed product stream; and
recycling part of the mixed product stream to the pressurized, pre-heated petroleum feedstock as a product recycle.

9. The process of claim 8, wherein the product recycle is split in a 1:1 ratio with a product stream.

10. The process of claim 8, wherein the supercritical water reactor is a two-stage reactor, the two-stage reactor comprising a first stage and a second stage, wherein a ratio of a residence time of the first stage to a residence time of the second stage is between 1.2:1 and 20:1.

11. The process of claim 10, wherein a temperature difference between the first stage and the second stage of the two-stage reactor is between 5° C. and 100° C.

12. The process of claim 10, wherein the first stage of the two-stage reactor is an upflow reactor and wherein the second stage of the two-stage reactor is a downflow reactor.

13. The process of claim 8, wherein the modified stream has a higher content of the aromatics and a lower content of impurities as compared to the pressurized, pre-heated petroleum feedstock.

* * * * *